United States Patent [19]

LeBlanc, Jr. et al.

[11] 4,066,646

[45] Jan. 3, 1978

[54] DIAGNOSTIC DEVICE AND HOUSING THEREFOR

[75] Inventors: Oliver H. LeBlanc, Jr.; William J. Ward, III, both of Schenectady, N.Y.

[73] Assignee: General Electric Company, Schenectady, N.Y.

[21] Appl. No.: 753,832

[22] Filed: Dec. 23, 1976

[51] Int. Cl.² ............... G01N 33/16; G01N 31/22; G01N 21/06
[52] U.S. Cl. .................. 23/259; 23/230 B; 23/253 TP
[58] Field of Search ........... 23/230 B, 253 TP, 259, 23/253 R; 424/12, 3; 195/127; 427/2, 4

[56] References Cited

U.S. PATENT DOCUMENTS

| 3,741,727 | 6/1973 | Stroterhoff | 23/253 TP |
| 3,826,619 | 7/1974 | Bratu, Jr. et al. | 23/253 TP |

*Primary Examiner*—R.E. Serwin

*Attorney, Agent, or Firm*—Leo I. MaLossi; Joseph T. Cohen; Jerome C. Squillaro

[57] ABSTRACT

A combined diagnostic device/housing combination is described. In its preferred application it is adapted to the detection of biological particles by the utilization of the phenomenon by which such biological particles interact specifically either immunologically or non-immunologically. The combination comprises a tube closed at one end, means (i.e., a cap) removably engageable with the opposite end of the tube to achieve sealing thereof such as to preclude the entry of microorganisms, a rod-like member affixed at one end thereof to the sealing means so as to project therefrom and a functional test device affixed to the free end of the rod-like member. When assembled, the rod-like member and test device are disposed within the tube and the tube is sealed ready for storage, shipping and/or use. Preferably, when the test device is for testing for specific biological particle interaction, the complete structure is made of glass and/or metal.

7 Claims, 1 Drawing Figure

U.S. Patent
Jan. 3, 1978
4,066,646
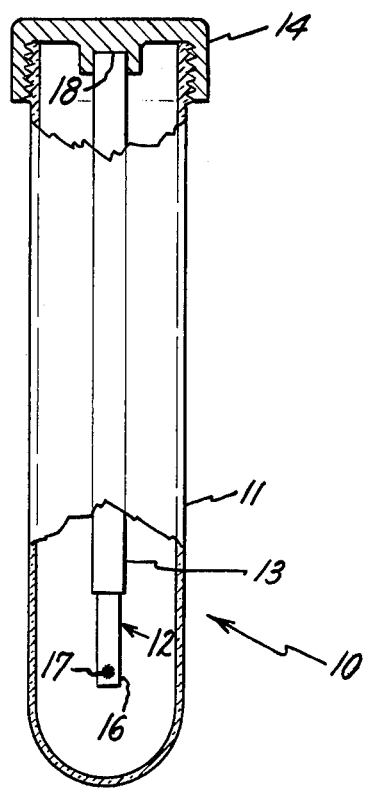

4,066,646

DIAGNOSTIC DEVICE AND HOUSING THEREFOR

BACKGROUND OF THE INVENTION

This invention relates to a device for clinical detection of biological particles in combination with a housing therefor. Detection is by the utilization of the phenomenon by which such biological particles interact specifically immunologically in the preferred construction.

Constructions of diagnostic devices for use in the immunological detection of proteins are disclosed in U.S. pat. application Ser. No. 384,113 — Giaever, filed July 30, 1973 (now abandoned) and U.S. Pat. No. 3,926,564 — Giaever. In both of these constructions the outer surface consists of a layer of preselected proteins specifically interactive with the protein of interest. In Ser. No. 384,113, the substrate surface to which the preselected protein layer is applied is preferably a metallic coating on a glass substrate. In U.S. Pat. No. 3,926,564, the surface to which the preselected protein layer is applied is made up predominately of metallic oxide, which metallic oxide may contain minute metallic particles. The aforementioned application was assigned to the assignee of this invention. Both the aforementioned Giaever patent and Giaever application are incorporated herein by reference.

In still another diagnostic device described and claimed in U.S. Pat. No. 3,979,184 — Giaever, a non-transparent surface of metal (solid metal or non-transparent coating of metal on a different substrate), which is a comparatively poor reflector of light, is covered with a thin transparent first layer of dielectric material. This first layer, in turn, has a transparent second layer of metal adhered over the outer surface thereof. U.S. Pat. No. 3,979,184 is also incorporated by reference.

Most antigens are proteins or contain proteins as an essential part, whereas all antibodies are proteins. Proteins are large molecules of high molecular weight, i.e., are polymers consisting of chains of variable numbers of amino acids. A given proteinaceous material will comprise entities (e.g., protein molecules, cells, etc.), which do not adhere to each other. Therefore, when a proteinaceous material is brought into contact with a substrate, it deposits as a single layer. If the entities are molecular in size, the resulting single layer is monomolecular. No other arbitrary protein will adhere to an already deposited protein layer. On the other hand, a protein that is specifically reactive relative to a protein that has been adsorbed onto the substrate will immunologically bond thereto. In accordance with the teachings of the above-cited applications, this discovery is exploited to provide medical diagnostic apparatus in which a substrate having a first layer of one protein adsorbed thereon is used to test suspected solutions for the presence of the protein specifically reactive thereto. If the specifically reactive protein is present in the solution, the slide (after exposure to the solution) will have a double protein layer thereon. If the specifically reactive protein be absent from the solution, the slide (after exposure to the solution) will have only the original layer thereon.

The term "biological particle" in intended to encompass smaller proteins (e.g., plasma proteins, antigens, antibodies, lactins) and bodies of proteinaceous material (e.g., viruses, bacteria, cells) capable of stimulating antibody producion, when injected into an animal, and/or having the property of interacting specifically either immunologically or non-immunologically.

The term "antigenic material" and the term "antigenically active material" describe material containing antigenic sites such as may be derived from viruses, bacteria, etc.

Reference herein to "visual readout" means readout that can be accomplished by a person with normal vision (or vision correctible to 20/40) who is not color blind and is unaided by instrumentation.

DESCRIPTION OF THE INVENTION

The diagnostic device/housing combination of this invention comprises a tube closed at one end, means (i.e., a cap) removably engageable with the opposite (open) end of the tube to achieve sealing thereof such as to preclude the entry of microorganisms, a rod-like member affixed at one end thereof to the sealing means so as to project therefrom and a functional test device affixed to the free end of the rod-like member. When assembled, the rod-like member and test device are disposed within the tube and the tube is sealed ready for storage, shipping and/or use.

BRIEF DESCRIPTION OF THE DRAWING

The subject matter of the instant invention for which protection is sought is presented as claims at the conclusion of the written description of the invention set forth herein. The description sets forth the manner and process of making and using the invention and the accompanying drawing sets forth a schematic representation of the assembled device and housing combination.

MANNER AND PROCESS OF MAKING AND USING THE INVENTION

As shown in the drawing diagnostic device/housing assembly 10 includes a tubular housing 11 open at one end. Housing 11 is of a length suitable for ease of handling, shipping and storage. It should also be of a diameter suitable for easily inserting and removing the detection device 12 and rod 13 to which it is affixed and for introducing and removing biological fluids. Rod 13 is affixed to, or is integrally formed with cap 14, which functions both as the support from which device 12 depends and also as the means for sealing housing 11. Cap 14 may engage housing 11 by commonly employed cap-to-tube fastening techniques, e.g., screw threads. Although a hermetic seal is preferred, in most instances it is only necessary to preclude the entry of microorganisms.

Housing 11, device 12, rod 13 and cap 14 are all to be made of materials, which are relatively inert, or at least non-reactive (e.g., plastics), with biological fluids.

Although this invention will be described herein in the form adapted to the detection of biological particles which interact specifically, device 12 and rod 13 may be adapted for other tests of biological fluids, e.g., urinalysis. Urinalysis is often conducted by the patient himself (as in the case of diabetics) and it is important to provide a test unit that is convenient to use and susceptible to minimum handling error.

In the case of assemblies in which device 12 is for the detection of biological particles, which interact specifically, preferably the housing 11, the substrate 16 for device 12, rod 13 and cap 14 are made entirely of glass and/or metal so that all parts of the assembly 10 can be easily cleaned to remove any surface-active contaminants prior to the deposition of layer 17 of biological particles specific to the select biological particles to be detected upon substrate 16.

The assembly of cap 14, rod 13 and substrate 16 is prepared so that rod 13 is affixed at one end to cap 14. Substrate 16 is attached to the distal end of rod 13. Thus, if rod 13 were made of metal a force fit or screw connection could be made between rod 13 and recess 18 in cap 14. Similarly, substrate 16 could be inserted into a tight-fitting slit (not shown) in the free end of rod 13. Attachment can be insured by forcing the sides of the slit against substrate 16. Once the assembly is prepared, the assembly and the inside of tube 11 are cleaned, layer 17 is applied, rod 13 (with test device 12 affixed thereto) is inserted into the properly cleansed tube 11 and cap 14 is placed in sealing engagement with the open end of tube 11. Depending upon the nature of the specific protein forming layer 17 it may be desirable to maintain the layer 17 bathed in a solution (e.g., saline or other liquid) during the interim between manufature and use of assembly 10. This is facilitated by the availability of tube 11 and cap 14 sealably engaged therewith.

At this stage the test device is maintainable free of contamination and is ready for storage and/or distribution to the point of use. In using this assembly 10, cap 14 (with rod 13 and device 12) is removed, tube 11 then serves as a container for the biological fluid (e.g., blood, serum, urine), which is to be tested. The rod/test device assembly is re-inserted, cap 14 is sealably engaged with tube 11 and contact is now provided between the biological fluid and layer 17. In this manner such contact may be maintained for the period required (e.g., during incubation) and the biological fluid can be agitated and/or heated. Thereafter, the cap 14 is disengaged and the rod/test device assembly is removed for rinsing, drying and readout (i.e., determination of the presence or absence of a bilayer of protein at location 17).

The specific construction of the test device 12 forms no part of this invention. In the case in which the test device is for the above-described detection of select biological particles, device 12 may, for example, be a thin strip of metal having a first preselected reflectivity, covered with an oxide layer and layer of specific protein to yield a second preselected reflectivity. The preparation of such a diagnostic device is described in U.S. patent application Ser. No. 752,186 - Healy et al. (Diagnostic Device and Manufacture Thereof), filed Dec. 20, 1976, and assigned to the assignee of the instant application. Other diagnostic device constructions as are described in the patents and application referred to in the Background of the Invention may also be used. By providing for the positive handling of test device 12 by its being affixed to rod 13, device 12 can be made smaller and for a lower initial cost than would be the case, if the test device would have to be directly held during testing and readout.

BEST MODE CONTEMPLATED

In the best mode contemplated for the detection of biological particles which interact specifically, the tube 11 would be made of glass having an interior diameter of about 1 cm. The screw cap 14, rod 13 and substrate 16 would be of metal and the combined lengths of rod 13 and substrate 16, when assembled, would be such relative to the length of tube 11 that area 17 will be disposed about 1 cm from the bottom. At this location protein layer 17 will make contact with a 1 cc sample disposed in the tube.

Preferably the test device 12 employs a short, narrow titanium sheet 10 mils thick as the substrate and an anodized layer about 300 A thick. The surface of the test device is nonspecularly reflecting, when prepared as described in the aforementioned Healy et al. application. After conduct of the immunological detection, visual readout of the test device 12 will disclose whether or not a second layer comprising the select biological particles is present.

For those applications in which the testing requires that the tube be heated, the tube should be made of heat-resistant glass, e.g., Pyrex. Preferably the protein layer will consist of a layer of antigenically active material although specific antibody layers (or layers of other biological particles) can be employed, if desired.

What we claim as new and desire to secure by Letters Patent of the United States is:

1. A diagnostic device and housing therefor comprising in combination:
    an imperforate tubular member closed at one end;
    means removably engageable with the open end of said tubular member for sealing said open end;
    a functional test device interconnected with said sealing means and spaced therefrom, said test device comprising a specific protein layer on a metallic substrate; and
    a longitudinally extending member interconnecting said sealing means and said test device, said member being affixed to both said sealing means and said test device.

2. The diagnostic device/housing combination recited in claim 1 wherein a glass tubular member is used in combination with metallic sealing means, a metallic interconnecting member and the metallic substrate bearing the protein layer.

3. The diagnostic device/housing combination recited in claim 1 wherein the interior surface of the tubular member and the surfaces of the sealing means, metal substrate and longitudinally-extending member are free of surface-active materials except for the specific protein layer.

4. The diagnostic device/housing combination recited in claim 1 wherein the protein layer is a layer of antigenically active material.

5. The diagnostic device/housing combination recited in claim 1 wherein the specific protein layer is located within about 1 centimeter from the closed end of the tubular member in the assembled combination.

6. The diagnostic device/housing combination recited in claim 1 wherein the engagement between the sealing means and the tubular member produces a hermetic seal.

7. The diagnostic device/housing combination recited in claim 1 wherein the sealing means is a screw-cap having a rod-like member affixed to the inside thereof and depending therefrom, said rod-like member in turn having the test device affixed thereto and depending therefrom.

* * * * *